United States Patent [19]

Mierau et al.

[11] Patent Number: 4,698,869
[45] Date of Patent: Oct. 13, 1987

[54] TOOTHBRUSH

[75] Inventors: Hans-Dieter Mierau; Thomas Spindler, both of Würzburg, Fed. Rep. of Germany

[73] Assignee: Blendax-Werke R. Schneider GmbH & Co., Fed. Rep. of Germany

[21] Appl. No.: 722,827

[22] Filed: Apr. 12, 1985

[30] Foreign Application Priority Data

Apr. 18, 1984 [DE] Fed. Rep. of Germany ....... 3414623

[51] Int. Cl.$^4$ .............................................. A46B 13/02
[52] U.S. Cl. .................................... 15/22 R; 15/105; 15/167 R
[58] Field of Search ................... 15/22 R, 22 A, 22 C, 15/23, 24, 167; 433/131, 118; 51/170 TL

[56] References Cited

U.S. PATENT DOCUMENTS

| 4,253,212 | 3/1981 | Fujita | 15/167 R |
| 4,450,599 | 5/1984 | Scheller et al. | 15/22 R |
| 4,476,604 | 10/1984 | White et al. | 15/167 R |

FOREIGN PATENT DOCUMENTS 0609238  2/1979  Switzerland ........................ 15/22 R Primary Examiner—Edward L. Roberts
Attorney, Agent, or Firm—Connolly and Hutz

[57] ABSTRACT

An electrically operated toothbrush comprises a housing with an electromotor inside the housing. The motor includes a rotatable shaft, means converting the rotary movement of the rotary shaft to an oscillatory movement of a brush support shaft which extends through the housing, and a toothbrush is attached to the free end of the support shaft outside of the housing. Sensing structure generates an impulse representative of the pressure exerted on the toothbrush during toothbrushing. A microprocessor or electronic device receives the impulses from the sensing structure during toothbrushing and compares those impulses with stored information representative of a predetermined optimum pressure range for toothbrushing. A signal transmittor releases a signal perceptible by the user of the toothbrush when the pressure on the toothbrush exceeds the predetermined optimum pressure range.

3 Claims, 3 Drawing Figures

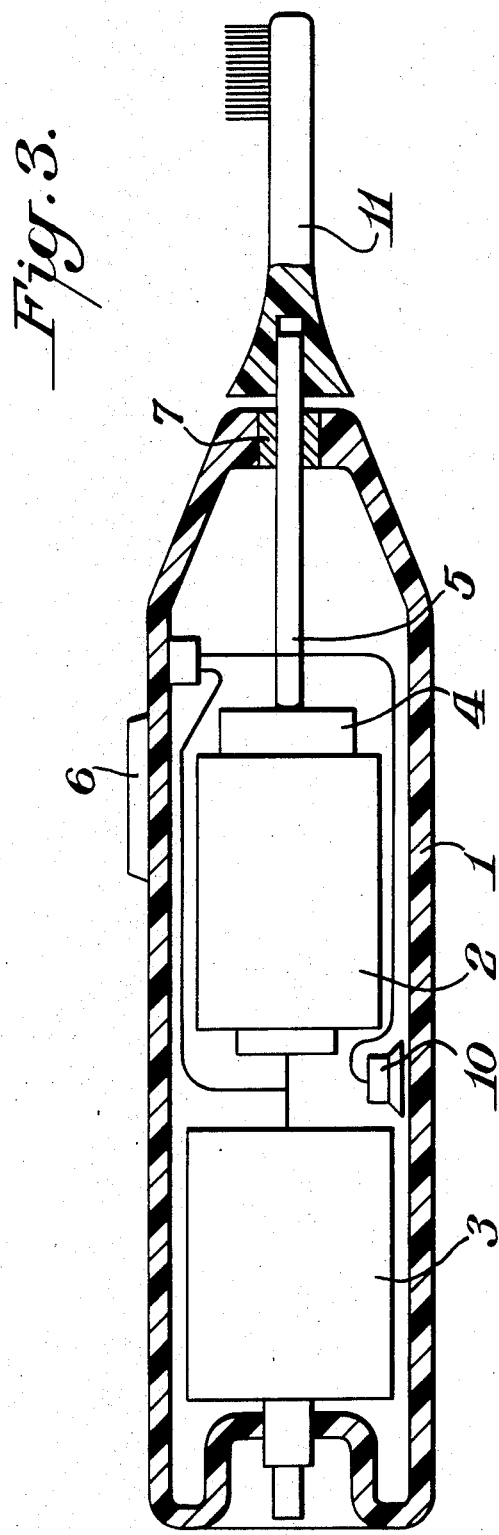

TOOTHBRUSH

The present invention relates to a toothbrush, particularly an electrically operated toothbrush, which allows the user to determine and observe the correct pressure when cleaning the teeth.

An essential criterion of the optimum function of a toothbrush, particularly an electric toothbrush, is the maintenance of a correct pressure when using the toothbrush. If the pressure is too low there is no sufficient cleaning. If the pressure is too high the gums are irritated resulting in bleeding of the gums and, as a long-term effect, probably even in a retrogression of the gingiva and exposure of the dentin. Thus, an essential condition for optimum toothbrushing, especially when using an electrically operated toothbrush, consists in cleaning with a correct pressure.

The present invention thus starts out from the problem to construct a toothbrush which allows the user to adjust the adequate pressure when using the brush and to maintain this pressure during toothbrushing.

The solution of this problem consists in providing a toothbrush, preferably an electrically operated toothbrush, whose construction is known per se, being fitted with an equipment for the optical or acoustical indication informing the user when leaving the optimum pressure during toothbrushing.

If an electrically operated toothbrush is used the construction is realized in the following way: A pressure sensor is fixed at the axle bearing provided for the incorporation of the brush shank which records the pressure effective at the slip-on brush and which is connected to a microprocessor, in which the optimum pressure range is recorded which is compared with the actual pressure value effective at the brush. The microprocessor is connected to a signal transmitter in such a way that in case of exceeding or remaining under the recorded optimum pressure range a perceptible signal is released.

In the case of a manual toothbrush the pressure is measured by strain gauges which are also connected to a microprocessor. In this case it is possible and also suitable to design the equipment for pressure measurement and signal release in such a way that it can be used for a great number of manual toothbrushes, i.e., it can be removed from the old brush and further used when the toothbrush is exchanged.

From German Pat. No. 3,117,160 an electrically operated toothbrush is already known which is supposed to allow the user a control of the brushing time. This is realized by the fact that this toothbrush is provided with a timer which controls the brushing time and which starts operating when the toothbrush is switched on, and with an indicator element; the timer, controlled by a load measurement equipment, should only work during that operating time in which a set strain is exerted on the bristle part and at the end of a set minimum operating time the timer releases a signal.

Thus, this known toothbrush has nothing in common with the problem of and its solution by the present invention, i.e., to allow the observation of the optimum pressure during the use of the toothbrush and to indicate upward and downward deviations from a recorded optimum pressure range by means of a signal transmitter.

BRIEF DESCRIPTION OF THE DRAWING

Novel features and advantages in addition to those mentioned above will become apparent to those of ordinary skill in the art from a reading of the following detailed description in conjunction with the accompanying drawing wherein:

FIG. 3 is a view similar to FIG. 1 but illustrating another embodiment of the present invention.

DETAILED DESCRIPTION OF THE INVENTION

Figure 1:
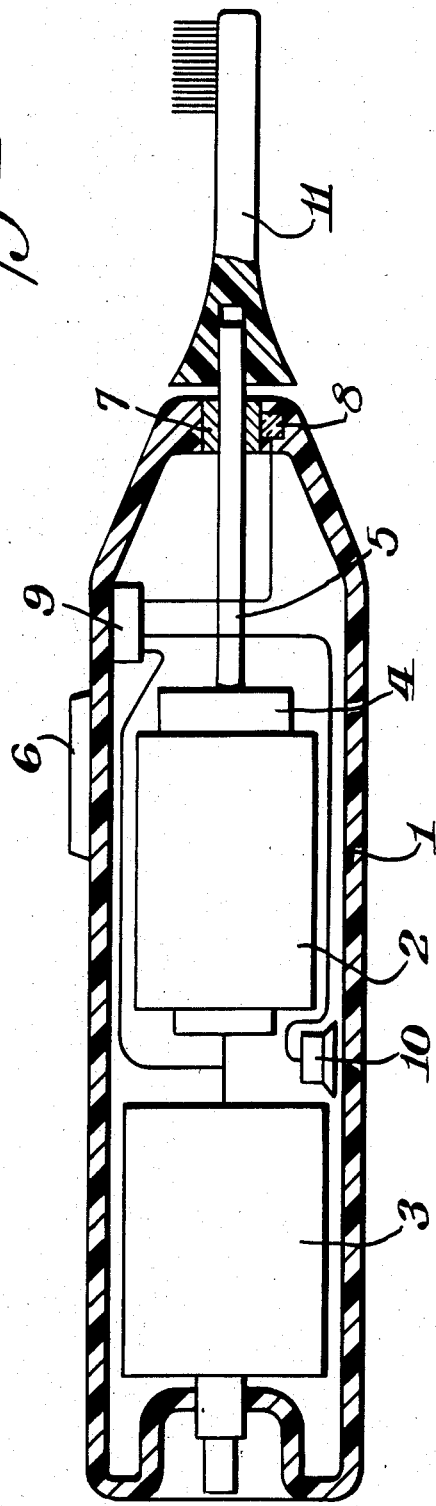
FIG. 1 is a side elevational view of an electrically operated toothbrush according to the present invention with portions thereof broken away to show interior detail.

In FIG. 1 an electrically operated toothbrush designed according to the invention is shown:

In a casing (1) there are housed an electromotor (2), an accumulator or a battery (3), a gear (4) for the conversion of the rotary movement of the motor into an oscillatory movement of the brush support shaft (5) and the slip-on brush (11), a switch (6) and the axle bearing (7).

A pressure sensor (8) at the bearing (7) records the effective pressure at the slip-on brush (11) and transmits it to a microprocessor (9).

In the microprocessor (9) an optimum pressure range is recorded which is compared with the actual pressure value effective at the brush. If both values are identical there is no reaction.

If the pressure at the slip-on brush (11) is higher or lower than the recorded optimum range, the microprocessor (9) releases an optical or acoustical signal, perceptible by the user, via a signal transmitter (10) which causes the user to change the pressure of the toothbrush against the teeth until the signal disappears.

Of course, it is also possible to adjust the equipment in such a way that the signal is kept on during the recorded optimum toothbrushing pressure and switches off when that pressure range is left.

Figure 2:
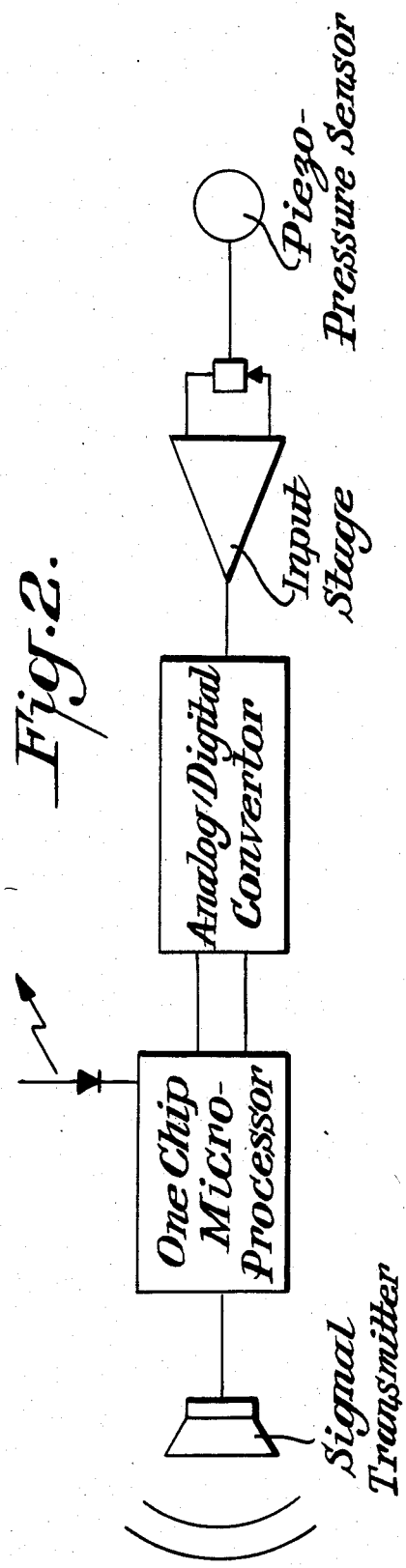
FIG. 2 is a diagrammatic view of the electrical control for the toothbrush of FIG. 1.

FIG. 2 shows the schematic construction of the above described loop control.

A further preferable embodiment of the invention is the measurement of the toothbrush pressure via the current consumption of the electromotor of the brush.

This method is based on the observation that a direct correlation exists between the pressure exerted during the use of the toothbrush and the current consumption of its electromotor: The higher the pressure, the higher the consumption and vice versa.

So by defining certain consumption ranges in relation to the desired pressure, undesired deviations may be indicated to the user by a signal transmitter.

FIG. 3 illustrates the above described embodiment of the invention wherein many of the components are similar to the components of the toothbrush shown in FIG. 1. Such similar components are identified by similar reference characters. In the embodiment of FIG. 3, current consumption of the electromotor is determined by electronic device 9 via a connecting line between such device and the electrical supply to the motor 2. When the current consumption of the electromotor exceeds a predetermined amount, the electronic device energizes the signal transmittor 10 which releases an

We claim:

1. An electrically operated toothbrush comprising a housing, a rotary motor within the housing, means converting the rotary movement of said motor to an oscillatory movement of a brush support shaft extending through the housing to a free end portion, toothbrush means at the free end portion of the brush support shaft, sensing means constructed and arranged to generate an impulse representative of the pressure exerted on the toothbrush means during toothbrushing, an electronic device connected to receive impulses from the sensing means during toothbrushing and to compare those impulses with stored information representative of a predetermined optimum pressure range for toothbrushing, and a signal transmittor connected to the electronic device arranged to release a signal perceptible by the toothbrush user when the pressure on the toothbrush exceeds the predetermined optimum pressure range.

2. An electrically operated toothbrush as in claim 1 including a bearing connected to support the brush support shaft, and wherein the sensing means is constructed and arranged to sense the pressure of the brush support shaft on the bearing and generate an impulse representative of that pressure.

3. An electrically operated toothbrush as in claim 1 wherein the sensing means is constructed and arranged to measure current consumption of the electromotor and generate an impulse representative of the pressure on the toothbrush causing such current consumption.

* * * * *